(12) United States Patent
Hwang et al.

(10) Patent No.: US 10,486,150 B2
(45) Date of Patent: Nov. 26, 2019

(54) CATALYST FOR OXIDATIVE DEHYDROGENATION AND METHOD OF PREPARING THE SAME

(71) Applicant: LG CHEM, LTD., Seoul (KR)

(72) Inventors: Sun Hwan Hwang, Daejeon (KR); Dong Hyun Ko, Daejeon (KR); Kyong Yong Cha, Daejeon (KR); Dae Heung Choi, Daejeon (KR); Myung Ji Suh, Daejeon (KR); Ye Seul Hwang, Daejeon (KR); Jun Kyu Han, Daejeon (KR); Seong Min Kim, Daejeon (KR); Jun Han Kang, Daejeon (KR); Joo Hyuck Lee, Daejeon (KR); Hyun Seok Nam, Daejeon (KR); Sang Jin Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 51 days.

(21) Appl. No.: 15/735,813

(22) PCT Filed: Dec. 21, 2016

(86) PCT No.: PCT/KR2016/015012
§ 371 (c)(1),
(2) Date: Dec. 12, 2017

(87) PCT Pub. No.: WO2017/164492
PCT Pub. Date: Sep. 28, 2017

(65) Prior Publication Data
US 2019/0184388 A1    Jun. 20, 2019

(30) Foreign Application Priority Data
Mar. 25, 2016 (KR) .................. 10-2016-0036238

(51) Int. Cl.
*B01J 37/03* (2006.01)
*B01J 23/06* (2006.01)
(Continued)

(52) U.S. Cl.
CPC ............. *B01J 37/031* (2013.01); *B01J 23/06* (2013.01); *B01J 23/80* (2013.01); *B01J 37/009* (2013.01);
(Continued)

(58) Field of Classification Search
CPC .................................................................
B01J 37/031; B01J 23/06; B01J 23/80;
B01J 37/009; B01J 37/0236; B01J 37/04;
B01J 37/08; C07C 5/48
See application file for complete search history.

(56) References Cited

U.S. PATENT DOCUMENTS 4,066,565 A * 1/1978 Sasazawa ............... C01G 49/06
252/62.56
8,513,479 B2    8/2013 Chung et al.
(Continued)

FOREIGN PATENT DOCUMENTS

EP         3308854 A1    4/2018
KR      10-0847206       7/2008
(Continued)

OTHER PUBLICATIONS

Gibson, M. and J. Hightower, "Oxidative Dehydrogenation of Butenes over Magnesium Ferrite," Journal of Catalysis 41: 431-439 (1976).
(Continued)

*Primary Examiner* — Melvin C. Mayes
*Assistant Examiner* — Michael Forrest
(74) *Attorney, Agent, or Firm* — Dentons US LLP

(57) ABSTRACT

The present invention relates to a catalyst for oxidative dehydrogenation and a method of preparing the same. More
(Continued)

particularly, the present invention provides a catalyst for oxidative dehydrogenation allowing oxidative dehydrogenation reactivity to be secured while increasing a first pass yield, and a method of preparing the catalyst.

13 Claims, 2 Drawing Sheets

(51) Int. Cl.
*B01J 23/80* (2006.01)
*B01J 37/00* (2006.01)
*B01J 37/02* (2006.01)
*B01J 37/04* (2006.01)
*B01J 37/08* (2006.01)
*C07C 5/48* (2006.01)

(52) U.S. Cl.
CPC .......... *B01J 37/0236* (2013.01); *B01J 37/04* (2013.01); *B01J 37/08* (2013.01); *C07C 5/48* (2013.01); *C07C 2523/80* (2013.01)

(56) References Cited

U.S. PATENT DOCUMENTS

2010/0121123 A1* 5/2010 Chung .................. B01J 23/002
　　　　　　　　　　　　　　　　　　　　　585/629
2010/0280300 A1* 11/2010 Chung .................. B01J 23/002
　　　　　　　　　　　　　　　　　　　　　585/629
2013/0158325 A1 6/2013 Kwon et al.

FOREIGN PATENT DOCUMENTS

KR　10-2012-0009687　2/2012
WO　　2009/045002　4/2009

OTHER PUBLICATIONS

Toledo et al., "Oxidative dehydrogenation of 1-butene over Zn—Al ferrites," Journal of Molecular Catalysis A: Chemical 125: 53-62 (1997).
Toledo et al., "A Magnetically Ordered Non-Stoichiometric Zinc Ferrite for the Oxidative Dehydrogenation Reactions," Mat. Res. Soc. Symp. Proc. 676: Y3.5.1-5.6 (2001).

* cited by examiner

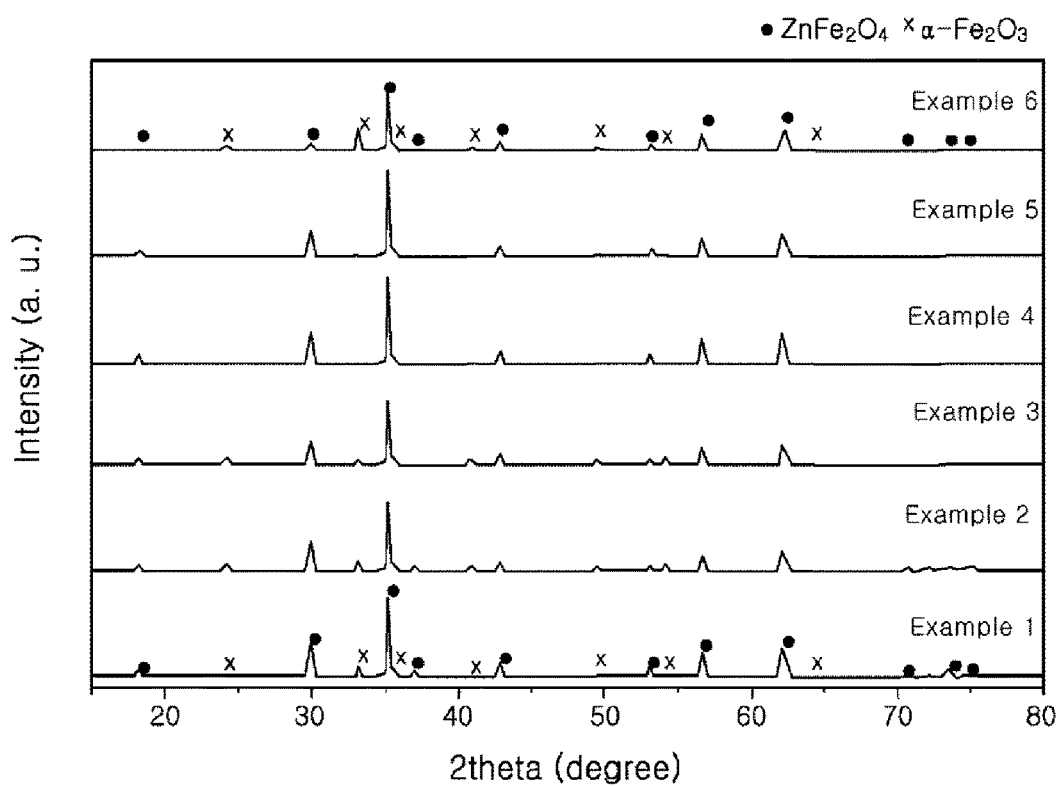
[FIG. 1]

[FIG. 2]
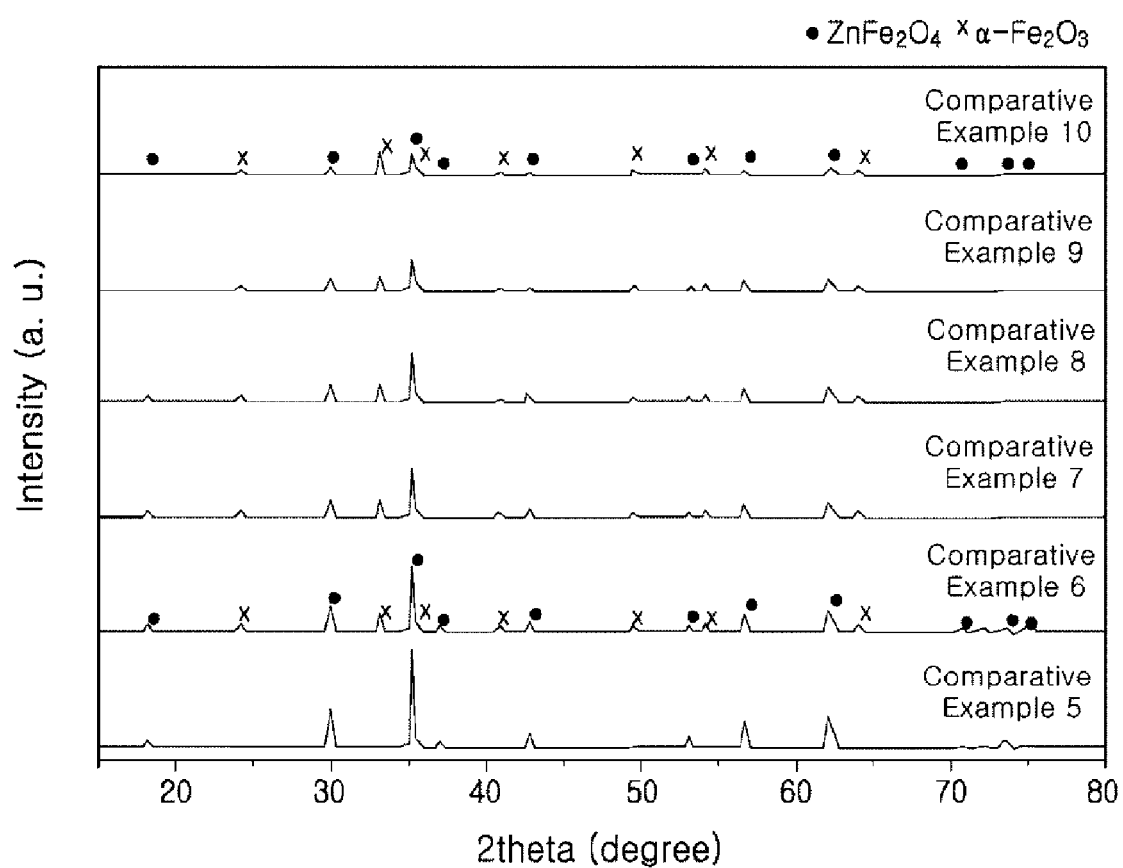

CATALYST FOR OXIDATIVE DEHYDROGENATION AND METHOD OF PREPARING THE SAME

CROSS-REFERENCE TO RELATED APPLICATION

This application is a National Stage Application of International Application No. PCT/KR2016/015012 filed on Dec. 21, 2016, which claims priority to and the benefit of Korean Patent Application No. 10-2016-0036238, filed on Mar. 25, 2016, in the Korean Intellectual Property Office, both of which are incorporated herein in their entirety by reference for all purposes as if fully set forth herein.

TECHNICAL FIELD

The present invention relates to a catalyst for oxidative dehydrogenation and a method of preparing the same. More particularly, the present invention relates to a catalyst for oxidative dehydrogenation allowing oxidative dehydrogenation reactivity to be secured while increasing a first pass yield, and a method of preparing the catalyst.

BACKGROUND ART

Demand for 1,3-butadiene, which is an intermediate in petrochemical products, and the value thereof are gradually increasing throughout the world. To produce such 1,3-butadiene, methods, such as naphtha cracking, direct butene dehydrogenation, and oxidative dehydrogenation of butene, have been used. However, in the case of naphtha cracking, energy consumption is high due to high reaction temperature. In addition, since naphtha cracking is not a process specifically designed for production of 1,3-butadiene production, other basic oils, other than 1,3-butadiene, are disadvantageously produced as surplus products. Meanwhile, direct dehydrogenation of normal-butene is thermodynamically unfavorable. In addition, since direct dehydrogenation of normal-butene is an endothermic reaction, high-temperature and low-pressure conditions are required to produce 1,3-butadiene in a high yield. Accordingly, direct dehydrogenation of normal-butene is not suitable as a commercial process for producing 1,3-butadiene.

Meanwhile, since, in the case of oxidative dehydrogenation of butene wherein butene reacts with oxygen in the presence of a metal oxide catalyst to generate 1,3-butadiene and water, stable water is generated and oxidative dehydrogenation of butene is thermodynamically advantageous. In addition, since oxidative dehydrogenation of butene is an exothermic reaction unlike direct dehydrogenation of butene, oxidative dehydrogenation of butene may produce 1,3-butadiene in a high yield even at low reaction temperature, compared to direct dehydrogenation of butene. In addition, since oxidative dehydrogenation of butene does not require additional heat supply, oxidative dehydrogenation of butene may be considered an effective production process that produces only 1,3-butadiene and thus satisfies demand for 1,3-butadiene.

The metal oxide catalyst is generally synthesized by a precipitation method. However, since a first pass yield of the metal oxide catalyst is small due to technical and spatial constraints, the same process is repeated several times to obtain a desired amount of the catalyst. Reactivity to a reactant of such catalysts prepared through several processes may be varied depending upon a preparation process pass, and such a reactivity difference between catalysts is directly related to the yield of a product (butadiene). Accordingly, it is an important research subject to reduce a reactivity difference between catalysts.

Therefore, there is a need for a method of preparing a catalyst capable of providing an improved first pass yield without a reactivity difference between prepared catalysts.

Related Art Document

[Patent Document] (Patent Document 1) U.S. Pat. No. 8,513,479B2

DISCLOSURE

Technical Problem

Therefore, the present invention has been made in view of the above problems, and it is one object of the present invention to provide a catalyst for oxidative dehydrogenation allowing oxidative dehydrogenation reactivity to be secured while increasing a first pass yield, and a method of preparing the catalyst.

The above and other objects can be accomplished by the present disclosure described below.

Technical Solution

In accordance with one aspect of the present invention, provided is a method of preparing a catalyst for oxidative dehydrogenation, the method including a step of mixing a trivalent cation iron (Fe) precursor with a divalent cation metal (A) precursor to form a mixed aqueous solution at a concentration of greater than 16.5% by weight and less than 53.5% by weight;

a step of feeding the mixed aqueous solution dropwise along with a basic aqueous solution into a coprecipitation tank, which contains distilled water at greater than 0° C. and less than 40° C. and has a pH of greater than 6 and less than 10, at a dripping rate of 2 g/min or more and less than 32 g/min to obtain a coprecipitation solution including $AFe_2O_4$ and $Fe_2O_3$ present together therein;

a step of filtering the coprecipitation solution to obtain a coprecipitate; and a step of firing the coprecipitate to obtain an $AFe_2O_4$—$Fe_2O_3$ product.

In accordance with another aspect of the present invention, provided is a method of preparing a catalyst for oxidative dehydrogenation, the method including a step of mixing a trivalent cation iron (Fe) precursor with a divalent cation metal (A) precursor to form a mixed aqueous solution at a concentration of 23% by weight to 35% by weight;

a step of feeding the mixed aqueous solution dropwise along with a basic aqueous solution into a coprecipitation tank, which contains distilled water at 5° C. to 30° C. in an amount of 0.5 times or more and less than 3 times the content (weight) of distilled water included in the mixed aqueous solution and has a pH of 8 to 9, at a dripping rate of 2 g/min to 10 g/min to obtain a coprecipitation solution including $AFe_2O_4$ and $Fe_2O_3$ present together therein;

a step of filtering the coprecipitation solution to obtain a coprecipitate; and a step of firing the coprecipitate to obtain an $AFe_2O_4$—$Fe_2O_3$ product.

In accordance with yet another aspect of the present invention, provided is a catalyst for oxidative dehydrogenation, including an $AFe_2O_4$ structure and an $Fe_2O_3$ structure, wherein A is one or more selected from the group consisting of copper (Cu), radium (Ra), barium (Ba), strontium (Sr), calcium (Ca), beryllium (Be), zinc (Zn), magnesium (Mg), manganese (Mn), and cobalt (Co), wherein the $AFe_2O_4$ structure is included in an amount of 20 to 99% by weight, and the $Fe_2O_3$ structure is included in an amount of 1 to 80% by weight.

Advantageous Effects

As apparent from the fore-going, the present invention advantageously provides a method for preparing a catalyst which adjusts the concentration of a mixed aqueous solution including a trivalent iron cation precursor and a divalent cation metal precursor to synthesize the mixed aqueous solution at high concentration, thereby increasing a first pass yield, reducing a waste water discharge amount, and providing a catalyst having improved reactivity. In addition, a catalyst according to the present invention is applicable to a fixed bed reactor, a mobile bed reactor, and a fluid bed reactor, and has very broad usability.

DESCRIPTION OF DRAWINGS

FIG. 1 illustrates XRD data of $ZnFe_2O_4$ structures and α-$Fe_2O_3$a structures of zinc ferrite catalysts prepared according to Examples 1 to 6.

FIG. 2 illustrates XRD data of $ZnFe_2O_4$ structures and α-$Fe_2O_3$a structures of zinc ferrite catalysts prepared according to Comparative Examples 5 to 10.

BEST MODE

To overcome technical and spatial constraints of a conventional method of preparing a catalyst for oxidative dehydrogenation discussed in the background art section, the present inventors developed a method for preparing a catalyst which adjusts the concentration of a mixed aqueous solution including a trivalent iron cation precursor and a divalent cation metal precursor to synthesize the mixed aqueous solution at high concentration, thereby increasing a first pass yield, reducing a waste water discharge amount, and providing a catalyst having improved reactivity, thus completing the present invention.

The catalyst for oxidative dehydrogenation of the present invention may be prepared according to the following processes.

In step 1, the trivalent cation iron (Fe) precursor and the divalent cation metal (A) precursor are mixed, thereby forming greater than 16.5% by weight and less than 53.5% by weight of a mixed aqueous solution.

The trivalent cation iron (Fe) precursor and the divalent cation metal precursor may be each independently, for example, one or more selected from the group consisting of a nitrate, an ammonium salt, a sulfate, and a chloride. In terms of cost, obtainability, and mass catalyst production cost, a nitrate or a chloride is preferred.

The divalent cation metal (A) may be, for example, one or more selected from the group consisting of copper (Cu), radium (Ra), barium (Ba), strontium (Sr), calcium (Ca), beryllium (Be), zinc (Zn), magnesium (Mg), manganese (Mn), and cobalt (Co), and is preferably zinc (Zn) or manganese (Mn).

With regard to the catalyst for oxidative dehydrogenation of the present invention, it is important to obtain a coprecipitate through ion exchange between iron and a divalent cation metal. Accordingly, a powder is not suitable for dispersion of iron and divalent cations, and has difficulty in generating a desired active material. On the other hand, since a mixed aqueous solution is a liquid, ion exchange between iron and a divalent cation metal is facilitated and, accordingly, a desired coprecipitate may be easily prepared.

With regard to a proper mixing ratio between an iron precursor and a divalent cation metal precursor in an aqueous solution, the trivalent cation iron (Fe) precursor is generally used in an amount of 1.5 to 10 mol, 1.5 to 4 mol or 1.5 to 2.5 mol based on 1 mol of the divalent cation metal (A) precursor. Within this range, a desired active material may be generated.

The mixed aqueous solution may be present at a concentration of greater than 16.5% by weight and less than 53.5% by weight, 18% by weight to 50% by weight, 20% by weight to 40% by weight, or 23% by weight to 35% by weight. Within this range, reactivity of the catalyst for oxidative dehydrogenation may be improved while greatly increasing a first pass yield.

The mixed aqueous solution may be prepared using, for example, 10% by weight to 30% by weight, 10% by weight to 25% by weight, 15% by weight to 25% by weight, or 20 to 25% by weight of the trivalent cation iron (Fe) precursor and 3% by weight to 10% by weight, 3% by weight to 8% by weight, 4 to 7% by weight, or 4 to 6% by weight of the divalent cation metal precursor in 60% by weight to 87% by weight, 67% by weight to 87% by weight, 68% by weight to 81% by weight, or 71% by weight to 76% by weight of distilled water.

The mixed aqueous solution may have, for example, a pH of 0 to 4, 1 to 3, or 1 to 2. Within this range, desired active ingredients may be stably generated during synthesis of a catalyst.

In step 2, the mixed aqueous solution is fed dropwise along with a basic aqueous solution into a coprecipitation tank containing distilled water and having adjusted pH, thereby obtaining a coprecipitation solution in which $AFe_2O_4$ and $Fe_2O_3$ are present together. The expression "is fed dropwise" refers to, for example, feeding dropwise two or more kinds of solutions to the same position or container.

As the distilled water, distilled water at greater than 0° C. and less than 40° C., greater than 0° C. to 30° C., or 5° C. to 25° C. may be supplied. Within this range, a first pass yield is increased and the content of an active catalyst is adjusted, whereby selectivity and yield of butadiene according to oxidative dehydrogenation become superior.

In an embodiment, the distilled water may be supplied in a content of 0.5 times or more, 0.5 times or more and less than 3 times, or 0.5 times or more and less than twice the weight of distilled water included in the mixed aqueous solution in step 1. Within this range, a first pass yield is increased, the pH of the coprecipitation solution is constantly maintained, and a discharge amount of waste water generated during a preparation process is reduced.

As the distilled water, for example, aqueous solutions of various basic substances, such as sodium hydroxide or ammonia, may be used, whereby the pH of the coprecipitation tank may be previously adjusted. Each of the basic aqueous solutions may be present at concentration of 0.001 to 0.01% by weight, 0.001 to 0.008% by weight, or 0.003 to 0.007% by weight. These basic aqueous solutions reduce a width of pH variation due to addition of the mixed aqueous solution at an initial catalyst synthesis step, thereby allowing production of a catalyst having a uniform composition.

The pH of the coprecipitation tank may be adjusted to, for example, greater than 6 and less than 11, 7 to less than 11, 8 to 10, or 8 to 9. Within this range, the content of $AFe_2O_4$ may be adjusted in a predetermined range when the mixed aqueous solution is added dropwise.

The aqueous precursor solution may be fed dropwise into a coprecipitation tank at a rate of 2 g/min or more, 2 g/min or more and less than 32 g/min, 2 g/min to 10 g/min, or 2 g/min to 7 g/min. Within this range, a first pass yield is increased and the content of an active ingredient is adjusted in a predetermined range, whereby selectivity and yield of butadiene according to oxidative dehydrogenation become superior.

The basic aqueous solution, which is supplied separately from the aqueous precursor solution, is not specified so long as it is, for example, an aqueous solution of each of various basic substances such as sodium hydroxide and ammonia. The concentration of the basic aqueous solution may be, for example, 10 to 35% by weight, 20 to 33% by weight, or 25 to 30% by weight. Within this range, the pH of the coprecipitation solution may be properly maintained.

The pH of the coprecipitation solution may be maintained, for example, at 7 or more and less than 11, 8 to 10, or 8 to 9. Within this range, a first pass yield of the coprecipitate is increased and selectivity and yield of butadiene according to oxidative dehydrogenation become superior.

The coprecipitation solution obtained in step 2 may be further subjected to a stirring step; an aging step; or a stirring and aging step, before performing filtration in step 3. In this case, coprecipitation of the precursors in the coprecipitation solution may be sufficiently carried out.

Each of the stirring and aging steps may be carried out, for example, for 30 minutes to 3 hours, 30 minutes to 2 hours, or 30 minutes to 1 hour and 30 minutes.

In step 3, the coprecipitation solution is filtered to obtain a coprecipitate.

The filtration is not specifically limited so long as it is a method generally used in the art. The filtration may be, for example, vacuum filtration. As a specific example, the coprecipitation solution may be filtered under a reduced pressure of 100 to 300 mbar, or 160 to 250 mbar. After the filtration, the coprecipitation may be washed, as needed.

After the filtration, a washing process is performed, waste water is discharged, and a coprecipitate is obtained as a solid. Due to the catalyst synthesis process performed at high concentration, a discharge amount of waste water generated in step 2 is reduced.

The coprecipitate may be dried at 60 to 100° C., 70 to 100° C., or 80 to 100° C. for 12 to 20 hours, 14 to 20 hours, or 14 to 18 hours by means of a general dryer. The solid may be provided in various forms such as a powder, the shape of a mold, or a film spread on a substrate.

In step 4, the coprecipitate is fired to obtain an $AFe_2O_4$—$Fe_2O_3$ product.

The filtered coprecipitate may be fired, for example, at 400 to 800° C., 500 to 800° C., or 550 to 750° C. for 1 to 10 hours, 3 to 8 hours, or 5 to 7 hours by means of a general firing furnace.

The filtered coprecipitate may be, for example, dried at 60 to 100° C., 70 to 100° C., or 80 to 100° C. for 12 to 20 hours, 14 to 20 hours, or 14 to 18 hours by means of a general dryer. In addition, the dried coprecipitate may be, for example, fired at 400 to 800° C., 500 to 800° C., or 550 to 750° C. for 1 to 10 hours, 3 to 8 hours, or 5 to 7 hours by means of a general firing furnace.

The firing may be carried out by a heat treatment method generally used in the art.

The catalyst for oxidative dehydrogenation of the present invention may also be prepared by the following processes.

That is, a trivalent cation iron (Fe) precursor is mixed with a divalent cation metal (A) precursor to form a mixed aqueous solution at a concentration of 23% by weight to 35% by weight.

The mixed aqueous solution dropwise is fed into along with a basic aqueous solution into a coprecipitation tank, which contains distilled water at 5° C. to 30° C. in an amount of 0.5 times or more and less than 3 times the content (weight) of distilled water included in the mixed aqueous solution and has a pH of 8 to 9, at a dripping rate of 2 g/min to 10 g/min to obtain a coprecipitation solution including $AFe_2O_4$ and $Fe_2O_3$ present together therein.

The coprecipitation solution is filtered to obtain a coprecipitate.

The coprecipitate is fired to obtain an $AFe_2O_4$—$Fe_2O_3$ product.

In accordance with the aforementioned preparation methods, the present invention is characterized by using high-concentration synthesis instead of conventional low-concentration synthesis. Catalysts prepared according to the methods of the present invention include $AFe_2O_4$ and $Fe_2O_3$ present together therein. Accordingly, when the catalysts are used in oxidative dehydrogenation, a conversion rate is improved while improving selectivity of a product, and side reactions are prevented.

That is, the present invention uses a simple method using high-concentration synthesis instead of low-concentration synthesis. Accordingly, when the catalyst of the present invention is used for oxidative dehydrogenation, reactivity of the catalyst is improved while increasing a unit production amount thereof for one process.

The catalyst for oxidative dehydrogenation according to the present invention includes an $AFe_2O_4$ structure and an $Fe_2O_3$ structure. Here, A is one or more selected from the group consisting of copper (Cu), radium (Ra), barium (Ba), strontium (Sr), calcium (Ca), beryllium (Be), zinc (Zn), magnesium (Mg), manganese (Mn), and cobalt (Co), the $AFe_2O_4$ structure is included in an amount of 20 to 99% by weight, and the $Fe_2O_3$ structure is included in an amount of 1 to 80% by weight.

In an embodiment, the $AFe_2O_4$ structure may be included in an amount of 50 to 95% by weight, and the $Fe_2O_3$ structure may be included in an amount of 5 to 50% by weight.

In an embodiment, the $AFe_2O_4$ structure may be included in an amount of 83 to 95% by weight, and the $Fe_2O_3$ structure may be included in an amount of 5 to 17% by weight.

In an embodiment, the $AFe_2O_4$ structure may be included in an amount of 85 to 95% by weight, and the $Fe_2O_3$ structure may be included in an amount of 5 to 15% by weight.

The $AFe_2O_4$ structure may have a first peak having a maximum peak intensity in a range of 34.5° to 35.5°, a second peak having a second peak intensity in a range of 29.5° to 30.5°, and a third peak having a third peak intensity in a range of 62° to 63°, as a result of XRD analysis.

The $AFe_2O_4$ structure may be, for example, $ZnFe_2O_4$ or $MnFe_2O_4$.

The $Fe_2O_3$ structure may have a first peak having a maximum peak intensity in a range of 33° to 34°, a second peak having a second peak intensity in a range of 35° to 36°, and a third peak having a third peak intensity in a range of 53.5° to 54.5°, as a result of XRD analysis.

The $Fe_2O_3$ structure may be, for example, $\alpha$-$Fe_2O_3$.

The catalyst is applicable to a fixed bed reactor, mobile bed reactor, and fluid bed reactor for oxidative dehydrogenation, and has very broad usability as a catalyst.

Now, the present invention will be described in more detail with reference to the following preferred examples. However, these examples are provided for illustrative purposes only. Those skilled in the art will appreciate that various modifications, additions and substitutions are possible, without departing from the scope and spirit of the invention. Therefore, it is obvious that the modifications, additions and substitutions are within the scope of the present invention.

EXAMPLE

Examples 1 to 6

In Examples 1 to 6, zinc was used as divalent metal cations and a catalyst was prepared according to a high-concentration synthesis method.

Example 1

In step 1, 18.029 g of zinc chloride ($ZnCl_2$) and 71.495 g of ferric chloride ($FeCl_3$) was dissolved in 233.39 g of distilled water, thereby preparing 322.914 g of an aqueous metal precursor solution at pH 1 (the concentration of the precursor solution: 27.7% by weight). Here, a mole ratio of the metal ingredients included in the aqueous metal precursor solution was Fe:Zn=2:1.

In step 2, a 0.005% ammonia solution, based on % by weight, was added to 233.39 g of room-temperature (25° C.) distilled water, and a coprecipitation tank adjusted to pH 8 was equipped with an outlet for an aqueous metal precursor solution and an outlet for an aqueous ammonia solution. An aqueous ammonia solution (pH 13.6) at a concentration of 28 to 30% was supplied at room temperature through the aqueous ammonia solution outlet while adding the prepared aqueous metal precursor solution mixture dropwise at a rate of 2 g/min through the aqueous metal precursor solution outlet, thereby constantly maintaining the pH of a coprecipitation solution in the coprecipitation tank at 8.

After completing the addition of the aqueous metal precursor solution, the coprecipitation solution was stirred for 1 hour such that sufficient coprecipitation was achieved. After stopping the stirring, a precipitate was allowed to settle for 1 hour at room temperature until the precipitate was completely settled, whereby phase separation was accomplished.

In step 3, the coprecipitation solution was vacuum filtered under a pressure condition of 200 mbar by means of a vacuum filter, thereby obtaining a coprecipitate. The obtained coprecipitate was washed. Subsequently, waste water was discharged and drying was carried out at 90° C. for 16 hours.

In step 4, the dried coprecipitate was put into firing furnace and was thermally treated at 650° C. for 6 hours. As a result, a zinc ferrite catalyst was prepared.

Example 2

A zinc ferrite catalyst was prepared in the same manner as in Example 1, except that, in step 2, a precursor solution was added at a dripping rate of 7 g/min.

Example 3

A zinc ferrite catalyst was prepared in the same manner as in Example 1, except that, in step 2, a precursor solution was added at a dripping rate of 10 g/min.

Example 4

A zinc ferrite catalyst was prepared in the same manner as in Example 1, except that, in step 2, the temperature of water supplied to a coprecipitation tank was 5° C. instead of room temperature (25° C.).

Example 5

A zinc ferrite catalyst was prepared in the same manner as in Example 1, except that, in step 1, the concentration of a precursor solution was 35% instead of 27.7% (based on % by weight).

Example 6

A zinc ferrite catalyst was prepared in the same manner as in Example 1, except that, in step 1, the concentration of a precursor solution was 23% instead of 27.7% (based on % by weight).

Comparative Examples 1 to 5

In Comparative Examples 1 to 5, zinc was used as divalent metal cations and a catalyst was synthesized according to various low-concentration synthesis methods.

In particular, a zinc ferrite catalyst was prepared in the same manner as in Example 1, except that the contents of zinc chloride ($ZnCl_2$), ferric chloride ($FeCl_3$), and distilled water constituting an aqueous metal precursor solution prepared in step 1, the content of water supplied to a coprecipitation tank, and pH in a stirring step were used as summarized in Table 1 below.

TABLE 1

| Classification | | Example 1 | Comparative Example 1 | Comparative example 2 | Comparative example 3 | Comparative Example 4 | Comparative Example 5 |
|---|---|---|---|---|---|---|---|
| | Fe/Zn mole ratio | 2 | 1.5-2.5 | 2 | 2 | 2 | 2 |
| Precursor solution (unit: g) | $FeCl_3 \cdot 6H_2O$ | 71.495 | 5.61 | 5.61 | 5.61 | 22.4 | 47.662 |
| | $ZnCl_2$ | 18.029 | 1.42 | 1.42 | 1.42 | 5.66 | 12.019 |
| | Distilled water | 233.39 | 100 | 250 | 100 | 400 | 835.5 |
| | Precursor solution concentration (% by weight) | 27.7 | 6.57 | 2.74 | 6.57 | 6.56 | 6.67 |

TABLE 1-continued

| Classification | Example 1 | Comparative Example 1 | Comparative example 2 | Comparative example 3 | Comparative Example 4 | Comparative Example 5 |
|---|---|---|---|---|---|---|
| Water supplied to coprecipitation tank (unit: g) | 233.39 | 100 | 1000 | 100 | 1200 | 8500 |
| Maintained pH of coprecipitation solution in coprecipitation tank/pH upon stirring | 8/8 | 3-12/ 3-12 | 6-10/ 6-10 | 9/9 | 9/9 | 9/9 |

Comparative Examples 6 to 10

In the following comparative examples, zinc was used as divalent metal cations and a catalyst was prepared according to a high-concentration synthesis method. Comparative Example 6 used a high-concentration synthesis method 30 times higher than Comparative Example 5, and Comparative Examples 7 to 10 were carried out by varying conditions of the high-concentration synthesis method of Example 1.

Comparative Example 6

A zinc ferrite catalyst was prepared in the same manner as in Comparative Example 5, except that 71.495 g of $FeCl_3 \cdot 6H_2O$, 18.029 g of $ZnCl_2$, and 41.8 g of distilled water were used to prepare a 68.18% precursor solution based on % by weight in step 1, pH of a coprecipitation solution in a coprecipitation tank was maintained at 8, pH in a stirring step was also maintained at 8, and 425 g of water was supplied to the coprecipitation tank.

Comparative Example 7

A zinc ferrite catalyst was prepared in the same manner as in Example 1, except that, in step 2, a precursor solution was added at a dripping rate of 32 g/min.

Comparative Example 8

A zinc ferrite catalyst was prepared in the same manner as in Example 1, except that, in step 2, the temperature of water supplied to a coprecipitation tank was 40° C. instead of room temperature (25° C.).

Comparative Example 9

A zinc ferrite catalyst was prepared in the same manner as in Example 1, except that, in step 2, pH of a coprecipitation solution in a coprecipitation tank was maintained at 10.

Comparative Example 10

A zinc ferrite catalyst was prepared in the same manner as in Example 1, except that, in step 2, pH of a coprecipitation solution in a coprecipitation tank was maintained at 11.

Test Example

Using zinc ferrite catalysts according to Examples 1 to 6 and Comparative Examples 1 to 10, various tests were carried out as follows.

Test Example 1: XRD Test

To investigate the content and structure of each zinc ferrite catalyst, the zinc ferrite catalyst was subjected to XRD analysis. Results are illustrated in FIGS. 1 and 2. Referring to FIGS. 1 and 2, XRD analysis results of the zinc ferrite catalyst of Examples 1 to 6 (FIG. 1), the zinc ferrite catalysts of Comparative Examples 5 to 10 (FIG. 2) were as follows: an $AFe_2O_4$ structure had a first peak having a maximum peak intensity in a range of 34.5° to 35.5°, a second peak having a second peak intensity in a range of 29.5° to 30.5°, and a third peak having a third peak intensity in a range of 62° to 63°, and an $Fe_2O_3$ structure had a first peak having a maximum peak intensity in a range of 33° to 34°, a second peak having a second peak intensity in a range of 35° to 36°, and a third peak having a third peak intensity in a range of 53.5° to 54.5°, as a result of XRD analysis.

In particular, when Example 1 (concentration of precursor solution: 27.7% by weight) of FIG. 1 and Comparative Example 5 (concentration of aqueous precursor solution: 6.67% by weight) and Comparative Example 6 (concentration of aqueous precursor solution: 68.18% by weight) of FIG. 2 are compared to each other, it can be confirmed that, when the concentration of the precursor solution is too low (corresponding to Comparative Example 5) or too high (corresponding to Comparative Example 6), crystallinity of the $ZnFe_2O_4$ structure is decreased and the $Fe_2O_3$ structure increases.

In addition, when Example 1 (dripping rate of mixed aqueous solution: 2 g/min), Example 2 (dripping rate of mixed aqueous solution: 7 g/min), and Example 3 (dripping rate of mixed aqueous solution: 10 g/min) of FIG. 1 and Comparative Example 7 (dripping rate of mixed aqueous solution: 32 g/min) of FIG. 2 are compared to each other, it can be confirmed that crystallinity of the $ZnFe_2O_4$ structure is decreased and the $Fe_2O_3$ structure increases as a dripping rate of the precursor solution increases.

In addition, when Example 1 (temperature of water supplied to coprecipitation tank: 25° C.), Example 4 (temperature of water supplied to coprecipitation tank: 5° C.) of FIG. 1 and Comparative Example 8 (temperature of water supplied to coprecipitation tank: 40° C.) of FIG. 2 are compared to each other, it can be confirmed that, when the temperature of water supplied to the coprecipitation tank is outside a suitable temperature range, crystallinity of the $ZnFe_2O_4$ structure is decreased and the $Fe_2O_3$ structure increases.

In addition, when Example 1 (pH of coprecipitation solution: 8) of FIG. 1 and Comparative Example 6 (pH of coprecipitation solution: 8), Comparative Example 9 (pH of coprecipitation solution: 10), and Comparative Example 10 (pH of coprecipitation solution: 11) of FIG. 2 are compared to each other, it can be confirmed that the $Fe_2O_3$ structure increases as the pH of the coprecipitation solution increases, and the $ZnFe_2O_4$ structure is most abundantly formed in Example 1 in which the pH of the coprecipitation solution is 8.

From these results, it can be confirmed that the concentration of the precursor solution, a dripping rate of the precursor solution, the temperature of water supplied to the coprecipitation tank, and a maintained pH of the coprecipitation solution in the coprecipitation tank respectively affect the crystallinity of the $ZnFe_2O_4$ structure and the $Fe_2O_3$ structure.

The $ZnFe_2O_4$ structure contents and the $Fe_2O_3$ structure contents (% by weight) measured by XRD analysis are summarized in Table 2 below.

TABLE 2

| Classification | $ZnFe_2O_4$ structure | $Fe_2O_3$ structure |
| --- | --- | --- |
| Example 1 | 90 | 10 |
| Example 2 | 86.4 | 13.6 |
| Example 3 | 85 | 15 |
| Example 4 | 93 | 7 |
| Example 5 | 92.5 | 7.5 |
| Example 6 | 92.7 | 7.3 |
| Comparative Example 5 | 92.3 | 7.7 |
| Comparative Example 6 | 82.2 | 17.8 |
| Comparative Example 7 | 72.3 | 27.7 |
| Comparative Example 8 | 74.8 | 25.2 |
| Comparative Example 9 | 69.3 | 30.7 |
| Comparative Example 10 | 53.6 | 46.4 |

As shown in Table 2, it can be confirmed that, in Examples 1 to 6 and Comparative Examples 5 to 10, the content of the $ZnFe_2O_4$ structure is 20 to 99% by weight and the content of the $Fe_2O_3$ structure is 1 to 80% by weight.

In particular, it can be confirmed that, in Examples 1 to 6 according to the present invention, the content of the $ZnFe_2O_4$ structure is 75 to 95% by weight and the content of the $Fe_2O_3$ structure is 5 to 25% by weight. From this result, it can be confirmed that crystallinity of the $ZnFe_2O_4$ structure is remarkably increased.

Test Example 2: First Pass Yield Test

A first pass yield of the zinc ferrite catalyst synthesized according to a high-concentration synthesis method in Example 1 and first pass yields of the zinc ferrite catalysts synthesized according a low-concentration synthesis method in Comparative Examples 1 to 5 were compared to each other.

For easy comparison, a production amount (unit: mol) of the $ZnFe_2O_4$ structure with regard to each of the catalysts was measured in a reactor containing 9335.5 g of distilled water. Results are summarized in Table 3 below.

TABLE 3

| Classification | Example 1 | Comparative Example 1 | Comparative Example 2 | Comparative Example 3 | Comparative Example 4 | Comparative Example 5 | Comparative Example 6 |
| --- | --- | --- | --- | --- | --- | --- | --- |
| First pass yield based on $ZnFe_2O_4$ (mol) | 2.6 | 0.48 | 0.08 | 0.48 | 0.24 | 0.09 | 2.6 |

As shown in Table 3, it can be confirmed that the first pass yield of the catalyst according to Example 1 of the present invention is improved five times or more, or 33 times or more those of the catalysts according to Comparative Examples 1 to 5.

Test Example 3: Analysis Test for Elements in Synthesized Catalyst

The zinc ferrite catalyst synthesized in each of Examples 1 to 6 and Comparative Examples 5 to 10 was subjected to element analysis by means of an energy dispersive spectrometer (EDS). Results are summarized in Table 4 below.

TABLE 4

| Classification | Example 1 | Example 2 | Example 3 | Example 4 | Example 5 | Example 6 |
| --- | --- | --- | --- | --- | --- | --- |
| Fe | 73.61 | 73.76 | 74.16 | 70.07 | 70.16 | 69.37 |
| Zn | 26.39 | 26.24 | 25.84 | 9.93 | 20.84 | 30.63 |
| Fe/Zn | 2.79 | 2.81 | 2.84 | 2.34 | 2.35 | 2.26 |

| Classification | Comparative Example 5 | Comparative Example 6 | Comparative Example 7 | Comparative Example 8 | Comparative Example 9 | Comparative Example 10 |
| --- | --- | --- | --- | --- | --- | --- |
| Fe | 68.3 | 76.55 | 78.64 | 78.22 | 79.23 | 86.02 |
| Zn | 31.7 | 23.45 | 21.36 | 21.78 | 20.77 | 13.98 |
| Fe/Zn | 2.2 | 3.26 | 3.68 | 3.59 | 3.82 | 6.15 |

As shown in Table 4, it can be confirmed that the catalysts synthesized using the high-concentration precursor solutions according to Examples 1 to 6 of the present invention reach a desired Fe/Zn mole ratio (desired Fe/Zn mole ratio=2), compared to the catalysts synthesized using the high-concentration precursor solutions according to Comparative Examples 6 to 10.

Test Example 5: Oxidative Dehydrogenation

Using each of the zinc ferrite catalysts synthesized in Examples 1 and 4 and the zinc ferrite catalyst synthesized in Comparative Example 5, butadiene was generated through the following oxidative dehydrogenation. Results are summarized in Table 5 below.

A metal tubular reactor with a diameter of 1.8 cm was used as a reactor, and the catalyst prepared in the example or the comparative example was fixed to have a catalyst layer volume of 30 cc. A 2-butene mixture including 40% by weight of cis-2-butene and 60% by weight of trans-2-butene and oxygen were used as reactants, and nitrogen and steam were injected to the reactor. Mole ratios between the reactants were set to as follows: oxygen/butene: 0.75, steam/butene: 12, and nitrogen/butene: 3. Steam, produced by vaporizing water at 340° C. by means of a vaporizer, was injected along with the reactants into the reactor.

The amount of a butene mixture was adjusted to 0.625 cc/min by means of a mass flow rate controller for liquids, the amounts of oxygen and nitrogen were adjusted by means of a mass flow rate controller for gas, and the amount of steam was adjusted by controlling an injection rate thereof by means of a liquid pump. A gas hourly space velocity (GHSV) of the reactor was set to 500 h$^{-1}$, and reaction was carried out at temperature summarized in Table 5 under atmospheric pressure (pressure gauge: 0).

After reaction, a product was subjected to gas chromatography (GC) analysis, and a conversion rate (X) of each butene in the mixture, 1,3-butadiene selectivity (S-BD), 1,3-butadiene yield (Y), COx selectivity (S_COx), and other selectivity (S others) were calculated according to Equations 1 to 3 below:

Conversion rate (%)=(moles of reacted butene/moles of supplied butene)×100    [Equation 1]

Selectivity (%)=(moles of generated 1,3-butadiene or Cox/moles of reacted butene)×100    [Equation 2]

Yield (%)=(moles of generated 1,3-butadiene/moles of supplied butene)×100    [Equation 3]

TABLE 5

| Classification | T (° C.) | X | S BD | Y | S COx | S others |
|---|---|---|---|---|---|---|
| Example 1 | 330 | 77.43 | 89.06 | 68.96 | 9.80 | 1.14 |
| Example 4 | 320 | 80.61 | 88.85 | 71.62 | 10.38 | 0.77 |
| Comparative Example 5 | 337 | 71.90 | 91.56 | 65.83 | 7.01 | 1.43 |

As shown in Table 5, it can be confirmed that Examples 1 and 4 according to the present invention exhibit superior butene conversion rate and yield. For reference, it can be confirmed that a butene conversion rate and a yield in Example 4 (temperature of water supplied to coprecipitation tank: 5° C.) are superior than those of Example 1 (temperature of water supplied to coprecipitation tank: 25° C.).

Meanwhile, it can be confirmed that Comparative Example 5 in which a catalyst was used according to a low-concentration synthesis method exhibits poor butene conversion rate and butadiene yield.

In conclusion, by using the high-concentration catalyst, instead of a low-concentration catalyst, according to the present invention, a preparation process is simplified and, accordingly, there are advantages in terms of catalytic efficiency and costs. That is, a catalyst capable of maintaining catalytic reactivity while increasing a first pass yield may be prepared.

The invention claimed is:

1. A method of preparing a catalyst for oxidative dehydrogenation, the method comprising:
   mixing a trivalent cation iron (Fe) precursor with a divalent cation metal (A) precursor to form a mixed aqueous solution having a concentration of total dissolved solids of greater than 16.5% by weight and less than 53.5% by weight;
   feeding the mixed aqueous solution dropwise at a dripping rate of 2 g/min or more and less than 32 g/min along with a basic aqueous solution into a coprecipitation tank, which contains distilled water comprising from 0.001 wt % to 0.01 wt % of a basic substance at a temperature greater than 0° C. and less than 40° C. and that has a pH of greater than 6 and less than 10 to obtain a coprecipitation solution comprising AFe$_2$O$_4$ and Fe$_2$O$_3$ present together therein;
   filtering the coprecipitation solution to obtain a coprecipitate; and
   firing the coprecipitate to obtain an AFe$_2$O$_4$—Fe$_2$O$_3$ product.

2. The method according to claim 1, wherein the trivalent cation iron (Fe) precursor and the divalent cation metal precursor are each independently one or more selected from the group consisting of a nitrate, an ammonium salt, a sulfate, and a chloride.

3. The method according to claim 1, wherein the divalent cation metal (A) is one or more selected from the group consisting of copper (Cu), radium (Ra), barium (Ba), strontium (Sr), calcium (Ca), beryllium (Be), zinc (Zn), magnesium (Mg), manganese (Mn), and cobalt (Co).

4. The method according to claim 1, wherein the trivalent cation iron (Fe) precursor is comprised in an amount of 1.5 to 10 mol based on 1 mol of the divalent cation metal (A) precursor.

5. The method according to claim 1, wherein the mixed aqueous solution is prepared by dissolving 10 to 30% by weight of the trivalent cation iron (Fe) precursor and 3 to 10% by weight of the divalent cation metal (A) precursor in 60 to 87% by weight of distilled water.

6. The method according to claim 1, wherein pH of the mixed aqueous solution is 0 to 4.

7. The method according to claim 1, wherein pH of the coprecipitation solution in the coprecipitation tank is maintained at 7 or more and less than 10.

8. The method according to claim 1, further comprising, before filtering the coprecipitation solution:
   stirring the coprecipitation solution; or
   aging the coprecipitation solution; or
   a stirring and aging the coprecipitation solution.

9. A method of preparing a catalyst for oxidative dehydrogenation, the method comprising:
   mixing a trivalent cation iron (Fe) precursor with a divalent cation metal (A) precursor to form a mixed aqueous solution having a concentration of total dissolved solids of 23% by weight to 35% by weight;
   feeding the mixed aqueous solution dropwise at a dripping rate of 2 g/min to 10 g/min along with a basic aqueous solution into a coprecipitation tank that contains distilled water comprising from 0.001 wt % to 0.01 wt % of a basic substance at a pH of 8 to 9 and at a temperature of 5° C. to 30° C. in an amount of 0.5 times or more and less than 3 times a weight of distilled water contained in the mixed aqueous solution, to obtain a coprecipitation solution comprising $AFe_2O_4$ and $Fe_2O_3$ present together therein;

filtering the coprecipitation solution to obtain a coprecipitate; and firing the coprecipitate to obtain an $AFe_2O_4$—$Fe_2O_3$ product.

10. A catalyst for oxidative dehydrogenation, comprising an $AFe_2O_4$ structure and an $Fe_2O_3$ structure, wherein A is one or more selected from the group consisting of copper (Cu), radium (Ra), barium (Ba), strontium (Sr), calcium (Ca), beryllium (Be), zinc (Zn), magnesium (Mg), manganese (Mn), and cobalt (Co), wherein:

the $AFe_2O_4$ structure is present in an amount of 20 to 99% by weight;

and the $Fe_2O_3$ structure is present in an amount of 1 to 80% by weight; and the $AFe_2O_4$ structure has an X-ray diffraction pattern comprising a first peak having a maximum intensity, the first peak located in a range of 34.5° to 35.5°, a second peak having a second highest peak intensity, the second peak located in a range of 29.5° to 30.5°, and a third peak having a third highest peak intensity, the third peak located in a range of 62° to 63°.

11. The catalyst according to claim 10, wherein the $Fe_2O_3$ structure has an X-ray diffraction pattern comprising a first peak having a maximum peak intensity, the first peak located in a range of 33° to 34°, a second peak having a second highest peak intensity, the second peak located in a range of 35° to 36°, and a third peak having a third highest peak intensity, the third peak located in a range of 53.5° to 54.5°.

12. The catalyst according to claim 10, wherein the $AFe_2O_4$ structure is present in an amount of 75 to 95% by weight, and the $Fe_2O_3$ structure is present in an amount of 5 to 25% by weight.

13. The method of claim 1, wherein the basic aqueous solution added into the coprecipitation tank is a 20 wt % to 33 wt % basic aqueous solution.

* * * * *